US012656296B2

(12) United States Patent
Yuan et al.

(10) Patent No.: US 12,656,296 B2
(45) Date of Patent: Jun. 16, 2026

(54) MEMS-BASED ALCOHOL SENSOR AND INTELLIGENT DEVICE

(71) Applicant: SHENZHEN EVERBEST MACHINERY INDUSTRY CO., LTD., Guangdong (CN)

(72) Inventors: Jianmin Yuan, Guangdong (CN); Lianghua Song, Guangdong (CN)

(73) Assignee: SHENZHEN EVERBEST MACHINERY INDUSTRY CO., LTD., Shenzhen (CN)

( * ) Notice: Subject to any disclaimer, the term of this patent is extended or adjusted under 35 U.S.C. 154(b) by 338 days.

(21) Appl. No.: 18/035,508

(22) PCT Filed: Dec. 4, 2020

(86) PCT No.: PCT/CN2020/134081
§ 371 (c)(1),
(2) Date: May 4, 2023

(87) PCT Pub. No.: WO2022/116204
PCT Pub. Date: Jun. 9, 2022

(65) Prior Publication Data
US 2024/0019395 A1 Jan. 18, 2024

(51) Int. Cl.
*G01N 27/406* (2006.01)
*G01N 27/407* (2006.01)
*G01N 33/497* (2006.01)

(52) U.S. Cl.
CPC ..... *G01N 27/4065* (2013.01); *G01N 27/4067* (2013.01); *G01N 27/407* (2013.01); *G01N 33/4972* (2013.01)

(58) Field of Classification Search
CPC ........... G01N 27/4065; G01N 27/4067; G01N 27/407; G01N 33/4972; G01N 29/00
See application file for complete search history.

(56) References Cited

U.S. PATENT DOCUMENTS

2002/0069699 A1* 6/2002 Sato .......................... G01F 5/00
73/204.22
2006/0091007 A1* 5/2006 Inoue ................. G01N 27/4175
204/426
(Continued)

FOREIGN PATENT DOCUMENTS

CN 2658750 Y * 11/2004
CN 200986551 Y * 12/2007
(Continued)

OTHER PUBLICATIONS

He et al., English translation of CN2658750Y, 2004 (Year: 2004).*
(Continued)

*Primary Examiner* — Shizhi Qian
(74) *Attorney, Agent, or Firm* — Fideli Law PLLC; Qiang Li

(57) ABSTRACT

A MEMS-based alcohol sensor, comprising a MEMS technology-based alcohol measurement module, an MCU processor (12), a circuit substrate (10), and a housing (30) that covers the circuit substrate (10). The alcohol measurement module outputs a concentration signal to the MCU processor (12) by means of a sampling and amplification circuit module, the MCU processor (12) processes the concentration signal and then outputs an alcohol concentration value. The MEMS technology-based alcohol measurement module and the MCU processor (12) are integrated in the housing (30), so the entire alcohol sensor is small in size, and can be applied to a mobile phone, a wearable device, etc.

14 Claims, 4 Drawing Sheets

(56)          References Cited

U.S. PATENT DOCUMENTS

| | | | | |
|---|---|---|---|---|
| 2006/0191318 A1* | 8/2006 | McBride | ............ | G01N 33/0009 |
| | | | | 73/23.2 |
| 2011/0060554 A1* | 3/2011 | Lueck | .................... | G01D 3/032 |
| | | | | 702/189 |
| 2013/0181854 A1* | 7/2013 | Koyama | ............... | H03M 1/124 |
| | | | | 341/122 |
| 2013/0281873 A1* | 10/2013 | Evans | ................. | B60K 28/063 |
| | | | | 600/532 |
| 2013/0305808 A1* | 11/2013 | Yoo | .................... | G01N 33/4972 |
| | | | | 73/23.3 |
| 2014/0234172 A1* | 8/2014 | Burgi | .................... | G01N 33/98 |
| | | | | 422/84 |
| 2020/0245906 A1* | 8/2020 | Yang | .................... | A61B 5/1455 |

FOREIGN PATENT DOCUMENTS

| | | | | |
|---|---|---|---|---|
| CN | 201341166 Y | | 11/2009 | |
| CN | 204072100 U | | 1/2015 | |
| CN | 208488402 U | * | 2/2019 | |
| WO | WO-2015181835 A1 | * | 12/2015 | ......... G01N 33/4972 |

OTHER PUBLICATIONS

Ren, English translation of CN200986551Y, 2007 (Year: 2007).*
Jiang et al. English translation of CN 208488402U, 2019 (Year: 2019).*
International Search Report of PCT Patent Application No. PCT/CN2020/134081 issued on Aug. 26, 2021.

* cited by examiner

MEMS-BASED ALCOHOL SENSOR AND INTELLIGENT DEVICE

TECHNICAL FIELD

The present application relates to the technical field of intelligent devices, and more particularly to a MEMS-based alcohol sensor and an intelligent device.

Background Art

An alcohol sensor is a test tool used to measure an alcohol content of air exhaled from a human body, and is also a measurement tool used by a traffic police to determine whether a driver has drunk alcohol or how much alcohol the driver has drunk during law enforcement, so that traffic accidents can be effectively avoided. In addition, the alcohol sensor can also be applied in some high-risk areas or areas where work after drinking is prohibited.

In order to meet the signal requirements, a conventional alcohol sensor has a large volume and thus has limited applications. Generally, it is only used in a professional alcohol measurement instrument.

SUMMARY OF THE INVENTION

Technical Problems

An objective of the embodiments of the present application is to provide a MEMS-based alcohol sensor and an intelligent device, so as to solve the technical problem in the prior art of an alcohol sensor being large in size and having limited applications.

Solutions to the Problem

Technical Solutions

To achieve the foregoing objective, a technical solution adopted in the present application is to provide a MEMS-based alcohol sensor, comprising a MEMS technology-based alcohol measurement module, an MCU processor, a circuit substrate, and a housing that covers the circuit substrate. The alcohol measurement module outputs a concentration signal thereof to the MCU processor by means of a sampling and amplification circuit module, and the MCU processor processes the concentration signal and then outputs an alcohol concentration value.

Further, the housing is provided with a first accommodating cavity in communication with the outside, the alcohol measurement module is arranged in the first accommodating cavity, the bottom of the housing is provided with a second accommodating cavity, the MCU processor is located in the second accommodating cavity, and the second accommodating cavity is filled with a sealant for sealing the MCU processor.

Further, a switch transistor is connected in parallel to two ends of the alcohol measurement module, and the sampling and amplification circuit module is a current-type sampling and amplification circuit.

Further, the switch transistor is a P-type MOS transistor, and the current-type sampling and amplification circuit comprises an operational amplifier, a first capacitor, a first resistor, a second resistor, a third resistor and a fourth resistor, wherein a source electrode of the P-type MOS transistor and a non-inverting input end of the operational amplifier are both connected to one end of the alcohol measurement module, a drain electrode of the P-type MOS transistor is connected to the other end of the alcohol measurement module, an inverting input end of the operational amplifier is connected to the other end of the alcohol measurement module by means of the first resistor, a grid electrode of the P-type MOS transistor and a positive power supply of the operational amplifier are both connected to a power supply voltage (VDD), the grid electrode of the P-type MOS transistor is further grounded sequentially by means of the second resistor and the third resistor, and a connection point of the second resistor and the third resistor is also connected to the non-inverting input end of the operational amplifier; and the first capacitor and the fourth resistor are both connected in parallel between the inverting input end of the operational amplifier and an output end of the operational amplifier, and the output end of the operational amplifier is connected to an input end of the MCU processor by means of an RC circuit.

Further, the alcohol measurement module comprises a first solid electrolyte membrane arranged in the first accommodating cavity, a first catalyst wire arranged at a top surface of the first solid electrolyte membrane and electrically connected to the MCU processor, and a second catalyst wire arranged at a bottom surface of the first solid electrolyte membrane and electrically connected to the MCU processor.

Further, a membrane pressing plate is further arranged in the first accommodating cavity and located at the bottom of the first solid electrolyte membrane, the membrane pressing plate fixes the first solid electrolyte membrane, the first catalyst wire and the second catalyst wire in the accommodating cavity, and the membrane pressing plate is fixed in the accommodating cavity by means of a sealant.

Further, a second solid electrolyte membrane is further arranged in the accommodating cavity and located at the bottom of the first solid electrolyte membrane, and the second catalyst wire is located between the second solid electrolyte membrane and the first solid electrolyte membrane.

Further, the accommodating cavity comprises a bottom cavity, a top opening, and a channel in communication with the bottom cavity and the top step, the first solid electrolyte membrane is placed in the bottom cavity, a breathable film is arranged in the top opening, the channel is filled with air, a middle portion of the first catalyst wire directly faces the channel, and a top wall of the bottom cavity is pressed against the first catalyst wire.

Further, a heating apparatus is further arranged in the first accommodating cavity.

The present application further provides an intelligent device, comprising a main body in which the MEMS-based alcohol sensor as described above is arranged.

Beneficial Effects of the Invention

Beneficial Effects

The alcohol sensor provided by the present application has the following beneficial effects: compared with the prior art, the MEMS technology-based alcohol measurement module and the MCU processor are integrated in the housing in the present application, such an alcohol sensor can directly output a digital signal, a user can read data only by means of a digital interface, and there is no need to additionally design a circuit structure and micro-control software; and since the alcohol measurement module uses a MEMS technology, the overall size of the alcohol sensor is reduced, and the alcohol sensor can be applied to various scenarios, such as mobile phones and wearable devices.

BRIEF DESCRIPTION OF THE DRAWINGS

Brief Description of the Drawings

In order to more clearly describe the technical solutions in the embodiments of the present application, the drawings required for describing the embodiments or the prior art will be briefly described below. Apparently, the drawings in the following description merely show some of the embodiments of the present application, and those of ordinary skill in the art would have obtained other drawings according to these drawings without involving any inventive effort.

Figure 1:
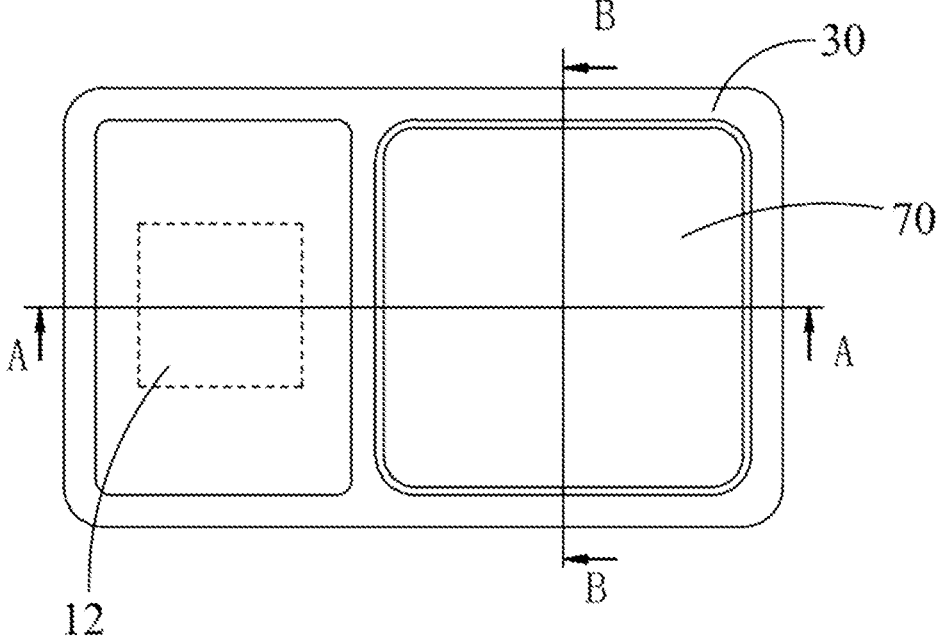
Figure 2:
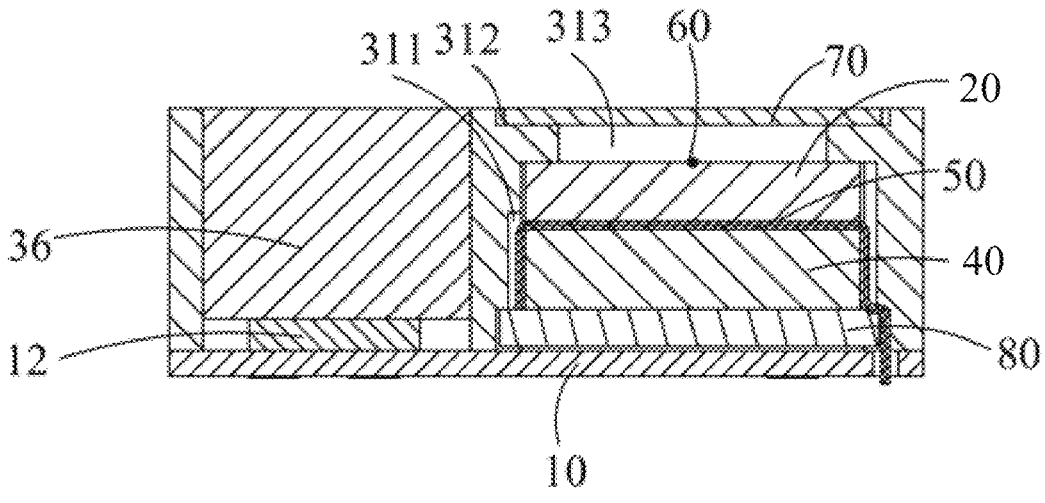
Figure 3:
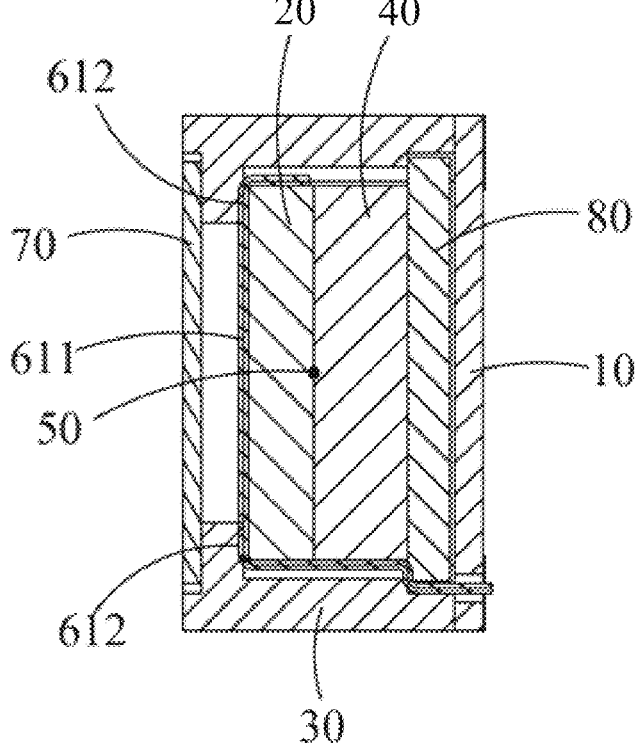
Figure 4:
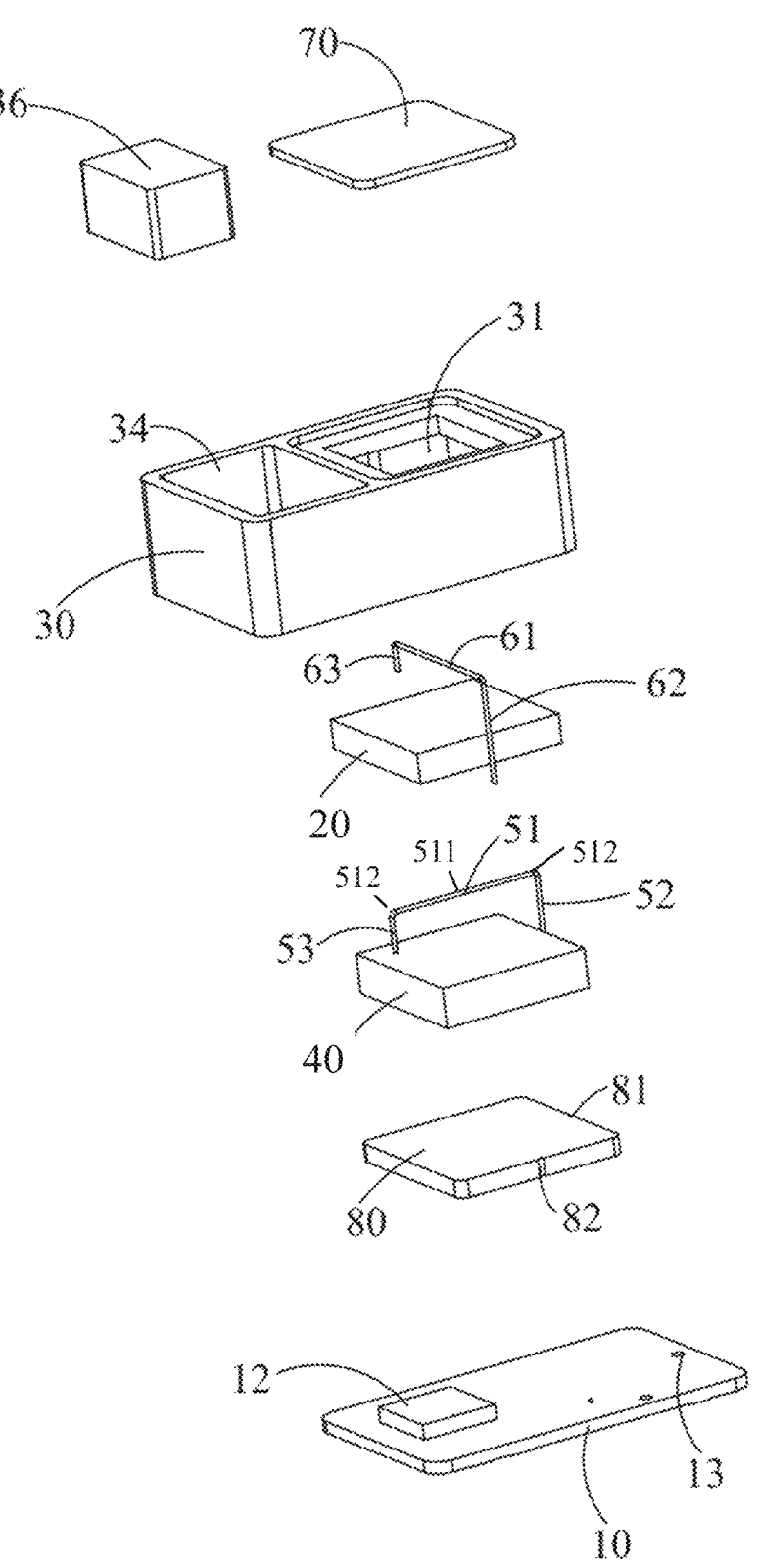
Figure 5:
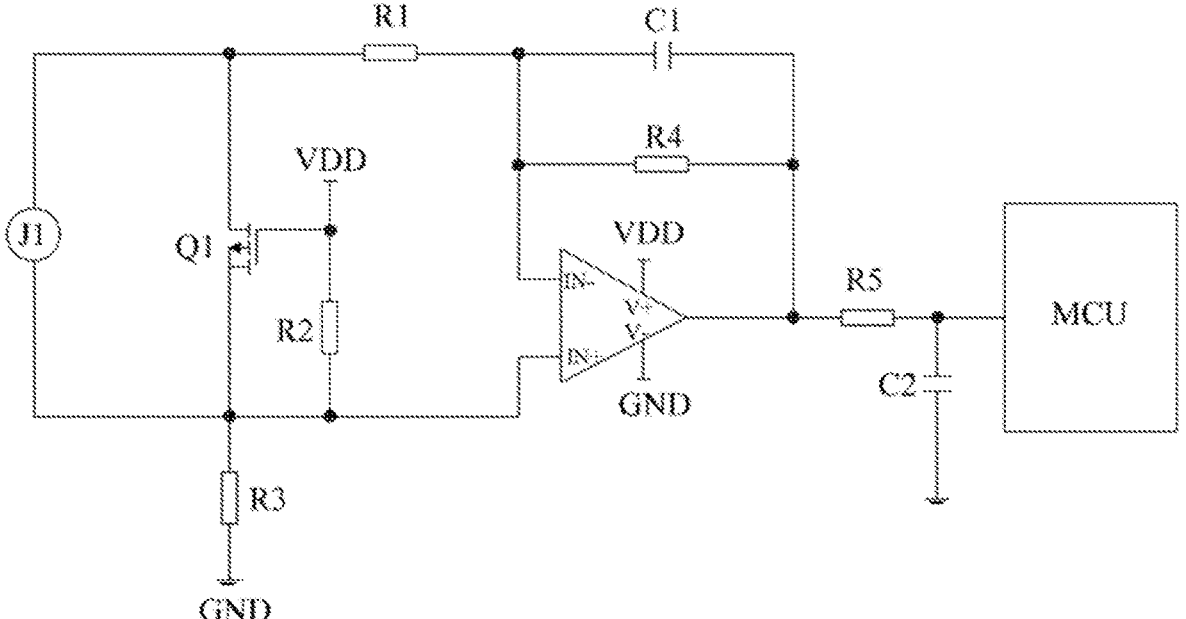

FIG. 1 is a top view of a MEMS-based alcohol sensor provided in an embodiment of the present application;

FIG. 2 is a cross-sectional view taken along line A-A in FIG. 1;

FIG. 3 is a cross-sectional view taken along line B-B in FIG. 1;

FIG. 4 is a schematic exploded view of a MEMS-based alcohol sensor provided in an embodiment of the present application; and FIG. 5 is a schematic diagram showing a circuit structure of a MEMS-based alcohol sensor provided in an embodiment of the present application.

Reference numerals in the drawings are as follows:

10—Circuit substrate; 12—MCU processor; 13—Welding hole; 20—First solid electrolyte membrane; 30—Housing; 31—First accommodating cavity; 34—Second accommodating cavity; 40—Second solid electrolyte membrane; 60—First catalyst wire; 61—First reaction portion; 62—First connection portion; 63—First fixing portion; 50—Second catalyst wire; 51—Second reaction portion; 52—Second connection portion; 53—Second fixing portion; 511—Middle portion of the second reaction portion; 512—Two ends of the second reaction portion; 70—Breathable film; 80—Membrane pressing plate; 82—First limiting groove; 81—Second limiting groove.

EMBODIMENTS OF THE INVENTION

Implementations of the Invention

In order to make the technical problems to be solved, the technical solutions, and the beneficial effects of the present application clearer, the present application will be described in further detail below with reference to the drawings and embodiments. It should be understood that the specific embodiments described herein are merely used to explain the present application and are not intended to limit the present application.

It should be noted that when an element is referred to as being "fixed to" or "arranged at" a further element, it can be directly located on the further element or indirectly located on the further element. When an element is referred to as being "connected to" a further element, it can be directly connected to the further element or indirectly connected to the further element.

It should be understood that the orientations or positional relationships indicated by the terms "length", "width", "upper", "lower", "front", "rear", "left", "right", "vertical", "horizontal", "top", "bottom", "inner", "outer", etc. are based on the orientations or positional relationships shown in the drawings, and are only for the convenience of describing the present application and simplifying the description, rather than indicating or implying that device or element referred to must have a specific orientation or be constructed and operated in a specific orientation, and therefore cannot be construed as limiting the present application.

In addition, the terms "first" and "second" are used for descriptive purposes only, and cannot be construed as indicating or implying relative importance or implicitly indicating the number of technical features indicated. Thus, the features defined with "first" and "second" can explicitly or implicitly include one or more of the features. In the description of the present application, the meaning of "a plurality of" is two or more, unless otherwise explicitly and specifically defined.

Referring to FIGS. 1 to 5, a MEMS-based alcohol sensor provided in an embodiment of the present application will be described below.

The MEMS-based alcohol sensor provided in this embodiment generally has a cuboid shape. The MEMS-based alcohol sensor comprises a circuit substrate 10, an MCU processor 12 arranged on the circuit substrate 10, and a housing 30 that covers the circuit substrate 10. The housing 30 is provided with a first accommodating cavity 31 in communication with the outside, an alcohol measurement module is arranged in the first accommodating cavity 31, the alcohol measurement module outputs a concentration signal thereof to the MCU processor 12 by means of a sampling and amplification circuit module, and the MCU processor 12 processes the concentration signal and an air pressure signal and then outputs an alcohol concentration value.

In the present application, the MEMS technology-based alcohol measurement module and the MCU processor 12 are integrated in the housing 30, such an alcohol sensor can directly output a digital signal, a user can read data only by means of a digital interface, and there is no need to additionally design a circuit structure and micro-control software; and since the alcohol measurement module uses a MEMS technology, the overall size of the alcohol sensor is reduced, and the alcohol sensor can be applied to various scenarios, such as mobile phones and wearable devices.

Referring to FIG. 4, the housing 30 is provided with a second accommodating cavity 34 at the bottom, and after the MCU processor 12 is placed on the circuit substrate 10 and located in the second accommodating cavity 34, the effects of fixing the MCU processor 12 and sealing the second accommodating cavity 34 are exerted by filling the second accommodating cavity 34 with a sealant 36, preventing the air from entering the second accommodating cavity 34, and ensuring that more air enters the first accommodating cavity 31 and reacts with the alcohol measurement module.

The alcohol measurement module in this embodiment is made based on the MEMS technology. MEMS (Micro-Electro-Mechanical System) is also called a micro-electro-mechanical system, a micro-system, a micro-machine, etc., which refers to a high-tech apparatus with the size of a few millimeters or even smaller. It is a miniature device or system that integrates a micro-sensor, a micro-actuator, a micro-mechanical structure, a micro-power supply, a signal processing and control circuit, a high-performance electronic integrated device, an interface, communications, etc. The alcohol measurement module in the present application is made based on the MEMS technology, has a small size and high accuracy, and can be applied in a variety of tiny scenarios.

Specifically, the alcohol measurement module located in the first accommodating cavity 31 comprises a first solid electrolyte membrane 20 arranged in the first accommodating cavity 31, a first catalyst wire 60 arranged at a top surface of the first solid electrolyte membrane 20 and electrically connected to the MCU processor 12, and a second catalyst wire 50 arranged at a bottom surface of the first solid electrolyte membrane 20 and electrically connected to the MCU processor 12.

In this embodiment, alcohol testing components such as the first solid electrolyte membrane 20, the first catalyst wire 60 and the second catalyst wire 50 are arranged in the compact housing 30, so that an internal structure of the alcohol sensor is more compact. In addition, the circuit substrate 10 may be used as a part of the bottom housing while achieving electrical connection, so that the entire height of the sensor is reduced, a lightweight and thin design can be better realized, the integration degree is also higher, and the alcohol sensor can be better applied to various smart devices.

Further, in this embodiment, a second solid electrolyte membrane 40 is further arranged in the first accommodating cavity 31 and located at the bottom of the first solid electrolyte membrane 20, and the second catalyst wire 50 is located between the second solid electrolyte membrane 40 and the first solid electrolyte membrane 20. With the provision of the two solid electrolyte membranes, the reaction effect of alcohol and the membranes and the catalyst wires is enhanced.

In this embodiment, the first solid electrolyte membrane 20 and the second solid electrolyte membrane 40 have a substantially square cross-section, which may be sized to be 4 mm*4 mm. Of course, the size of the solid electrolyte membranes may also be adjusted according to the overall size requirements of the alcohol sensor. As proton exchange membranes, the solid electrolyte membranes have good chemical resistance and good mechanical properties, so that the solid electrolyte membranes can be very thin to ensure the free movement of ions during the reaction, are acidic and can react with alcohol in the air.

The first catalyst wire 60 and the second catalyst wire 50 are substantially the same in structure, and may be structurally varied. For example, the first catalyst wire 60 and the second catalyst wire 50 may have an inverted L shape. That is, the first catalyst wire 60 comprises a horizontal first reaction portion 61 and a first connection portion 62 bent downwardly along the first reaction portion 61. The first reaction portion 61 is attached to the top surface of the first solid electrolyte membrane 20, and the first connection portion 62 extends out along a side surface of the first solid electrolyte membrane and is electrically connected to the circuit substrate 10. The second catalyst wire 50 comprises a horizontal second reaction portion 51 and a second connection portion 52 bent downwardly along the second reaction portion 51. The second reaction portion 51 is attached to the top surface of the second solid electrolyte membrane 40, and the second connection portion 52 extends out along a side surface of the second solid electrolyte membrane 40 and is electrically connected to the circuit substrate 10. During measurement, the air enters the top of the first accommodating cavity 31 and chemically reacts with the first solid electrolyte membrane 20 and the second solid electrolyte membrane 40 so as to generate sufficient electric charges, while the first catalyst wire 60 and the second catalyst wire 50 extend out as conductive electrodes and are electrically connected to the circuit substrate 10 so as to implement signal transmission.

During mounting, the two catalyst wires and the two solid electrolyte membranes are pressed against each other. The purpose is to fix the two catalyst wires more firmly, avoiding falling off. In this embodiment, the two catalysts have the structure as shown in FIG. 4.

The first catalyst wire 60 further comprises a first fixing portion 63 bent downwardly along an end of the first reaction portion 61. The first fixing portion 63 is attached to a side surface of the first solid electrolyte membrane 20 and is opposed to the first connection portion 62. The second catalyst wire 50 further comprises a second fixing portion 53 bent downwardly along an end of the second reaction portion 51. The second fixing portion 53 is attached to a side surface of the second solid electrolyte membrane 40 and is opposed to the second connection portion 52. In this way, during mounting, the first fixing portion 63 of the first catalyst wire 60 is hooked to one side surface of the first solid electrolyte membrane 20, and the first connection portion 62 extends out from the other opposite side surface of the first solid electrolyte membrane 20. Similarly, the second fixing portion 53 of the second catalyst wire 50 is hooked to one side surface of the second solid electrolyte membrane 40, and the second connection portion 52 extends out from the other opposite side surface of the second solid electrolyte membrane 40. With such a structure, the first catalyst wire 60 and the second catalyst wire 50 are more firmly mounted and are less likely to fall off.

Although there is no direct contact between the first catalyst wire 60 and the second catalyst wire 50, in this embodiment, the first catalyst wire 60 and the second catalyst wire 50 are spatially arranged crosswise, namely, the first reaction portion 61 and the second reaction portion 51 of the reaction portion are arranged in a cross manner, so that the first connection portion 62 and the second connection portion 52 can extend out from different side surfaces of the solid electrolyte membranes, avoiding short circuiting caused by mutual contact when they extend out from the same side surface. Of course, the first catalyst wire 60 and the second catalyst wire 50 may also be arranged in other manners, such as in a parallel or non-parallel manner. It is only required to ensure that the connection portions of the two catalyst wires are not in contact with each other.

In order to better fix the two solid electrolyte membranes and the two catalyst wires in the first accommodating cavity 31, in this embodiment, a membrane pressing plate 80 is further arranged in the first accommodating cavity 31 and located at the bottom of the first solid electrolyte membrane 20. During mounting, the housing 30 is first inverted, the second catalyst wire 50; and the second solid electrolyte membrane 40, the first catalyst wire 60 and the first solid electrolyte membrane 20 are sequentially placed into the housing, then pressed by the membrane pressing plate 80, and finally sealed and fixed by means of a sealant.

In this embodiment, since the membrane pressing plate 80 is provided at the bottom, in order to better allow the first catalyst wire 60 and the second catalyst wire 50 to extend out and be electrically connected to the circuit substrate 10, a first limiting groove 82 and a second limiting groove 81 are respectively formed in side walls of the membrane pressing plate 80, the first connection portion 62 of the first catalyst wire 60 downwardly extends out along the inside of the first limiting groove 82 and is electrically connected to the circuit substrate 10, and the second connection portion 52 of the second catalyst wire 50 downwardly extends out along the second limiting groove 81 and is electrically connected to the circuit substrate 10.

It can be seen from FIG. 2 to 4 that in this embodiment, the first accommodating cavity 31 passes through in a vertical direction, and can be divided into three parts according to the size of passage, namely, a bottom cavity 311, a top opening 312 and a channel 313 for communicating the bottom cavity 311 with the top opening 312. The membrane pressing plate 80, the first solid electrolyte membrane 20 and the second solid electrolyte membrane 40 are sequentially arranged in the bottom cavity 311, and the channel 313 located between the bottom cavity 311 and the top opening 312 is filled with air. In this way, it is ensured that the first solid electrolyte membrane 20 and the second solid electrolyte membrane 40 can be in sufficient contact with the air, thereby forming a sufficiently large current to ensure the testing accuracy. Moreover, in the above structure, a middle portion 511 of the second reaction portion 51 of the second catalyst wire 50 directly faces the channel 313, and a top wall of the bottom cavity 311 is pressed at two ends of the second reaction portion 51. In this way, the second reaction portion 51 of the second catalyst wire 50 can be in sufficient contact with the air in the channel 313 and the top opening 312, and the top wall of the bottom cavity 311 also functions a to press the two ends 512 of the second reaction portion 51 to some extent, so that better fixation can be achieved between the second catalyst wire 50 and the second solid electrolyte membrane 40.

In this embodiment, the top opening 312 is a depressed stepped hole formed in the top surface of the housing 30, the breathable film 70 is arranged on a stepped surface of the depressed stepped hole, and outside air can penetrate the breathable film 70 and reacts with the first solid electrolyte membrane 20, the first catalyst wire 60 and the second catalyst wire 50. The breathable film 70 can filter water vapor and dust from the air, and also has a good air permeability, ensuring the passing of clean air and making measurement more accurate. Of course, the breathable film 70 may also be omitted from the alcohol sensor in this embodiment, and when the alcohol sensor is specifically applied to various devices or apparatuses, providing the devices or apparatuses with a breathable film 70 can also provide water-proof, dust-proof and air-permeable functions. The depressed stepped bore has a square cross-section, and the channel 313 and the bottom cavity 311 that are in communication therewith also have square cross-sections. With the square top opening, an air inlet can be maximized in a limited area such that a sufficient amount of intake air can be effectively guaranteed, a miniature alcohol sensor will not have a smaller signal than a conventional alcohol sensor; and the square first accommodating cavity 31 is large in size, facilitating the chemical reaction of alcohol with the two catalyst wires and the two solid electrolyte membranes.

Further, in this embodiment, a heating device (not shown) is further arranged in the first accommodating cavity 31. The heating device may specifically be a heating sheet, and after testing, the air with alcohol can be volatilized quickly by heating the first accommodating cavity 31, so that there is no residual air in the first accommodating cavity 31, namely, the alcohol in the first accommodating cavity 31 is also cleared to ensure the accuracy of a next test.

In this embodiment, the material of the first catalyst wire 60 and the second catalyst wire 50 is a noble metal. Specifically, the noble metal may be a platinum wire. Of course, other noble metals may be used to make the catalyst wires.

In this embodiment, the circuit substrate 10 comprises a circuit substrate 11 and components (not shown) arranged on the circuit substrate. Two welding holes 13 are formed in the circuit substrate 11, and the first catalyst wire 60 and the second catalyst wire 50 are respectively welded to the two welding holes 13 after extending out from the first limiting groove 82 and the second limiting groove 81.

Furthermore, in this embodiment, a sampled signal acquired by the alcohol measurement module is processed by a current-type amplification circuit. Referring to a schematic diagram showing a circuit structure of FIG. 5, a switch transistor is connected in parallel to two ends of the alcohol measurement module, and is a P-type MOS transistor herein. The MOS transistor is opened during sampling, and the MOS transistor is closed to discharge the alcohol measurement module after sampling, so that the charge balance of the alcohol measurement module can be maintained when no measurement is performed. During a specific operation, when the alcohol measurement module samples an air containing a certain concentration of alcohol, the current will change, the current signal is converted into a voltage signal which is amplified and then sent to the MCU processor for processing, and finally a result is output in the form of a digital signal.

In an embodiment, the current-type sampling and amplification circuit comprises an operational amplifier U1, a first capacitor C1, a first resistor R1, a second resistor R2, a third resistor R3 and a fourth resistor R4. A source electrode of the P-type MOS transistor and a non-inverting input end IN+ of the operational amplifier U1 are both connected to one end of the alcohol measurement module J1, a drain electrode of the P-type MOS transistor is connected to the other end of the alcohol measurement module J1, and the other end of the alcohol measurement module J1 is further connected to an inverting input end IN− of the operational amplifier U1 by means of the first resistor R1. A grid electrode of the P-type MOS transistor and a positive power supply of the operational amplifier are both connected to a power supply VDD, the grid electrode of the P-type MOS transistor is further grounded sequentially by means of the second resistor R2 and the third resistor R3, and a connection point of the second resistor R2 and the third resistor R3 is also connected to the non-inverting input end IN+ of the operational amplifier U1. The first capacitor C1 and the fourth resistor R4 are both connected in parallel between the inverting input end IN− of the operational amplifier U1 and an output end OUT of the operational amplifier, and the output end OUT of the operational amplifier U1 is connected to an input end of the MCU processor by means of an RC circuit.

In this embodiment, the MCU processor is a single chip microcomputer, and the input end of the MCU processor is an analogue input signal end. The operational amplifier U1 converts the current signal output from the alcohol measurement module J1 into a voltage signal which is amplified and then sent to the analog input signal end of the single chip microcomputer. In addition, the MOS transistor Q1 is opened at the time of sampling of the alcohol measurement module J1, and the MOS transistor Q1 is closed to discharge the alcohol measurement module J1 after sampling, so that the charge balance of the alcohol measurement module J1 can be maintained when no measurement is performed. The operational amplifier U1 is an operational amplifier having a high amplification factor.

Since the sampled signal is a weak signal, the principle of inverting amplification with a single power supply VCC is adopted, and a bias voltage is set at the non-inverting input end and can be adjusted. The signal of the alcohol measurement module J1 is processed by the sampling and amplification circuit and then sent to the analog input signal end of the MCU processor through an RC circuit.

When the alcohol measurement module J1 samples an air containing a certain concentration of alcohol, the current will change, the sampled current signal is converted into a voltage signal which is amplified and then sent to the MCU processor for processing, the voltage signal is processed by the MCU processor to obtain an alcohol concentration value, and this concentration data is output through a digital interface of the single chip microcomputer, so that the data of this sensor can be read from the outside by means of a processor or other smart communication devices.

The present application further provides an intelligent device (not shown), comprising a main body in which the MEMS-based alcohol sensor as described above is arranged. Due to the small size and accurate testing, the alcohol sensor can be widely applied to mobile phones, or daily wearable devices, such as wristbands, watches and glasses.

The above embodiments are merely preferred embodiments of the present application but not intended to limit the present application, and any modifications, equivalent replacements, improvements, etc. made within the spirit and principle of the present application should be included within the scope of protection of the present application.

The invention claimed is:

1. A MEMS-based alcohol sensor, comprising: a MEMS technology-based alcohol measurement module, an MCU processor, a circuit substrate, and a housing that covers the circuit substrate, wherein the housing is provided with a first accommodating cavity to facilitate accommodation and communication, the alcohol measurement module is arranged in the first accommodating cavity, the alcohol measurement module outputs a concentration signal thereof to the MCU processor, the concentration signal is derived by a sampling and amplification circuit module, and the MCU processor processes the concentration signal and then outputs an alcohol concentration value, wherein the MEMS-based alcohol sensor is configured to directly output a digital signal readable by a digital interface with no need of an additional circuit or component, wherein the alcohol measurement module comprises a first solid electrolyte membrane arranged in the first accommodating cavity, a first catalyst wire arranged at a top surface of the first solid electrolyte membrane and electrically connected to the MCU processor, and a second catalyst wire arranged at a bottom surface of the first solid electrolyte membrane and electrically connected to the MCU processor, wherein a membrane pressing plate is further arranged in the first accommodating cavity and located at the bottom of the first solid electrolyte membrane, the membrane pressing plate fixes the first solid electrolyte membrane, the first catalyst wire and the second catalyst wire in the first accommodating cavity, and the membrane pressing plate is fixed in the first accommodating cavity by means of a sealant.

2. The MEMS-based alcohol sensor of claim 1, wherein the bottom of the housing is provided with a second accommodating cavity, the MCU processor is located in the second accommodating cavity, and the second accommodating cavity is filled with a sealant for sealing the MCU processor.

3. An intelligent device, comprising a main body, wherein the MEMS-based alcohol sensor of claim 2 is arranged in the main body.

4. The MEMS-based alcohol sensor of claim 1, wherein a switch transistor is connected in parallel to two ends of the alcohol measurement module, and the sampling and amplification circuit module is a current-type sampling and amplification circuit.

5. The MEMS-based alcohol sensor of claim 4, wherein the switch transistor is a P-type MOS transistor, and the current-type sampling and amplification circuit comprises an operational amplifier, a first capacitor, a first resistor, a second resistor, a third resistor and a fourth resistor, wherein a source electrode of the P-type MOS transistor and a non-inverting input end of the operational amplifier are both connected to one end of the alcohol measurement module, a drain electrode of the P-type MOS transistor is connected to the other end of the alcohol measurement module, an inverting input end of the operational amplifier is connected to the other end of the alcohol measurement module by means of the first resistor, a grid electrode of the P-type MOS transistor and a positive power supply of the operational amplifier are both connected to a power supply, the grid electrode of the P-type MOS transistor is further grounded sequentially by means of the second resistor and the third resistor, and a connection point of the second resistor and the third resistor is also connected to the non-inverting input end of the operational amplifier; and the first capacitor and the fourth resistor are both connected in parallel between the inverting input end of the operational amplifier and an output end of the operational amplifier, and the output end of the operational amplifier is connected to an input end of the MCU processor by means of an RC circuit.

6. An intelligent device, comprising a main body, wherein the MEMS-based alcohol sensor of claim 5 is arranged in the main body.

7. An intelligent device, comprising a main body, wherein the MEMS-based alcohol sensor of claim 4 is arranged in the main body.

8. The MEMS-based alcohol sensor of claim 1, wherein a second solid electrolyte membrane is further arranged in the first accommodating cavity and located at the bottom of the first solid electrolyte membrane, and the second catalyst wire is located between the second solid electrolyte membrane and the first solid electrolyte membrane.

9. An intelligent device, comprising a main body, wherein the MEMS-based alcohol sensor of claim 8 is arranged in the main body.

10. The MEMS-based alcohol sensor of claim 1, wherein the first accommodating cavity comprises a bottom cavity, a top opening, and a channel in communication with the bottom cavity and the top opening, the first solid electrolyte membrane is placed in the bottom cavity, a breathable film is arranged in the top opening, the channel is filled with air, and a top wall of the bottom cavity is pressed against the first catalyst wire.

11. An intelligent device, comprising a main body, wherein the MEMS-based alcohol sensor of claim 10 is arranged in the main body.

12. The MEMS-based alcohol sensor of claim 1, wherein a heating apparatus is further arranged in the first accommodating cavity.

13. An intelligent device, comprising a main body, wherein the MEMS-based alcohol sensor of claim 12 is arranged in the main body.

14. An intelligent device, comprising a main body, wherein the MEMS-based alcohol sensor of claim 1 is arranged in the main body.

* * * * *